United States Patent [19]

Michaelis et al.

[11] 4,147,666
[45] Apr. 3, 1979

[54] ADDITIVES FOR LUBRICANTS

[75] Inventors: Klaus P. Michaelis, Lindenfels, Odenwald; Hermann O. Wirth, Bensheim-Auerbach, both of Fed. Rep. of Germany

[73] Assignee: Ciba-Geigy AG, Basel, Switzerland

[21] Appl. No.: 836,939

[22] Filed: Sep. 27, 1977

[30] Foreign Application Priority Data

Oct. 6, 1976 [CH] Switzerland ............... 12638/76

[51] Int. Cl.$^2$ ............... C10M 1/38; C10M 3/32; C10M 5/28; C07C 149/00
[52] U.S. Cl. ............... 252/48.2; 260/609 R; 260/608; 260/609 PD; 260/609 F
[58] Field of Search ............... 252/48.2; 260/609 R, 260/608

[56] References Cited

U.S. PATENT DOCUMENTS

| | | | |
|---|---|---|---|
| 2,619,508 | 11/1952 | Mikeska et al. | 252/42.7 |
| 3,211,651 | 10/1965 | Elliott et al. | 252/46.7 |
| 3,361,723 | 1/1968 | Ephraim | 260/79 |
| 3,906,048 | 9/1975 | Vanlerberghe et al. | 260/609 R |
| 4,031,023 | 6/1977 | Musser et al. | 252/48.2 |
| 4,053,422 | 10/1977 | Walker | 252/48.2 |

Primary Examiner—Irving Vaughn
Attorney, Agent, or Firm—Luther A. R. Hall

[57] ABSTRACT

Compounds of the general formula I, and mixtures thereof,

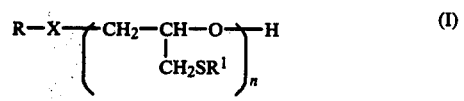

in which R is linear alkyl having 12 to 24 C atoms, branched alkyl having 8 to 30 C atoms or alkylated phenyl or phenyl-alkyl having 8 to 24 C atoms, X is an oxygen or sulphur atom, n is a value from 0.5 to 8 or an integer from 1 to 8 and $R^1$ is a hydrogen atom or a radical of the formula

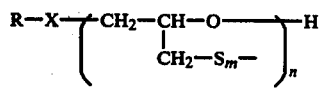

in which m is 0 or integers from 1 to 3, are excellent extreme-pressure additives in lubricants.

14 Claims, No Drawings

ADDITIVES FOR LUBRICANTS

The present invention relates to mercaptans, thioethers, disulphides and polysulphides and their use as additives for lubricants and also to the lubricants provided with these additives.

Polyethers which contain mercapto groups and are synthesised from monofunctional or polyfunctional alcohols and epichlorohydrin by further reacting the reaction products thereof with $H_2S$ or alkali metal bisulphides in order to replace the Cl atoms, are known from U.S. Pat. No. 3,361,723. These compounds are used as intermediates for the preparation of epoxide resins. It has been found that the thiolic polyethers described in this American patent are not suitable as additives for lubricating oils since their solubility in the relevant lubricants is too low.

Various additives are generally added to lubricants in order to improve their characteristics in use. In particular, there is a need for additives which are intended to protect the devices to be lubricated from wear due to friction. The demands made upon such extreme-pressure additives for lubricants are that they are adequately soluble, that they increase the load-bearing capacity and that they do not have a corrosive action on the particular metal parts. The object of the present invention is to provide effective additives for lubricants, which meet these requirements.

The present invention relates to compounds of the general formula I, and mixtures thereof,

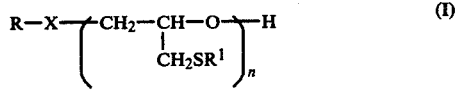

(I)

in which R is linear alkyl having 12 to 24 C atoms, branched alkyl having 8 to 30 C atoms or alkylated phenyl or phenyl-alkyl having 8 to 24 C atoms, X is an oxygen or sulphur atom, n is a value from 0.5 to 8 or an integer from 1 to 8 and $R^1$ is a hydrogen atom or a radical of the formula

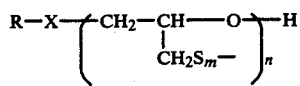

in which m is 0 or integers from 1 to 3. In the compounds of the formula I, X is preferably an oxygen atom, m is 1 or the number 1 and n is a value from 1 to 5, especially 1 to 3 and in particular 1.

Preferred sub-groups are those in which, in formula I, $R^1$ is a hydrogen atom or $R^1$ is a radical of the formula

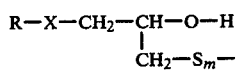

and in which m is 0 or 1 and n is 1, as well as mixtures thereof.

R in formula I is linear alkyl having 12 to 24 and preferably 16 to 24 C atoms. Examples which may be mentioned are: dodecyl, tridecyl, tetradecyl, pentadecyl, hexadecyl, octadecy, eicosyl, docosyl and tetracosyl.

R in formula I is, especially, branched alkyl which preferably contains 8 to 24, and especially 12 to 22, C atoms. Examples are: i-octyl, 2-propylpentyl, i-nonyl, i-decyl, 2-butylhexyl, 3-hexylpentyl, 3-methylundecyl, i-dodecyl, 2-methyldodecyl, 2-ethyldecyl, 3-propyldecyl, 2-hexyldecyl, i-hexadecyl, 2-ethylhexadecyl, i-octadecyl, i-eicosyl, 2-hexyltetradecyl, 2-ethyleicosyl and 2-butyloctadecyl.

Those branched alkyl radicals which are derived from industrial alcohols and alcohol mixtures are also suitable. These alcohols are generally produced by the Ziegler process from aluminum, hydrogen and ethylene with subsequent hydroxylation of the reaction product and are usually mixtures of different branched alcohols.

These alcohols are commercially obtainable, for example Guerbet alcohols and Alfols (manufacturer: Condea), Dobanols (manufacturer: Shell) and Oxanols (manufacturer: Ruhr-Chemie), and are a preferred group.

R in formula I can also be alkylated phenyl or phenyl-alkyl. The alkylene group in phenyl-alkyl contains preferably 1 to 3 C atoms and especially 1 C atom. The phenyl and phenyl-alkyl are preferably substituted by 1 to 2 alkyl groups which contain 4 to 18 C atoms and preferably are branched. Examples are: ethylphenyl, i-propylphenyl, t-butylphenyl, hexylphenyl, octylphenyl, t-octylphenyl, nonylphenyl, dodecylphenyl, octadecylphenyl, dimethylphenyl, di-nonylphenyl, methylbenzyl, ethylbenzyl, i-propylbenzyl, t-butylbenzyl, octylbenzyl, nonylbenzyl, dodecylbenzyl, dimethylbenzyl and dioctylbenzyl.

The compounds, according to the invention, of the formula I are obtained by processes similar or analogous to those described in U.S. Pat. No. 3,361,723, by reacting compounds of the formula II, or mixtures thereof,

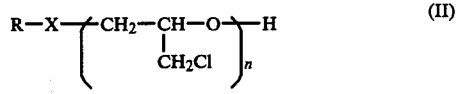

(II)

in which R, X and n are as defined, with hydrogen sulphide or di-alkali metal sulphides $Na_2S_x$ (x = 1–4) in at least stoichiometric amounts and removing from the reaction mixture the hydrogen chloride or the sodium chloride which is formed. The di-alkali metal sulphides are obtained in a known manner by dissolving sulphur in $Na_2S$.

The reaction is generally carried out at temperatures of up to 150° C. and preferably of 60° to 120° C. The reaction can be carried out under normal pressure or elevated pressure. When preparing the mercaptan derivatives ($R^1$ = H in formula I), $H_2S$ is used and the reaction is advantageously carried out under elevated pressure. In order to achieve a substantially complete reaction it is also advisable to use an excess of $H_2S$. The reaction can be carried out without or with a solvent. Suitable solvents are alcohols, especially methanol and ethanol.

In the case of the reaction with $H_2S$, an alkali metal hydroxide or alkaline earth metal hydroxide, especially NaOH, is preferably added in at least equimolar amounts, relative to the Cl content of the compound of the formula II.

In order to isolate the desired compounds, the reaction mixture is acidified and extracted with a suitable solvent, for example ethers, and the product is then further purified by means of conventional methods.

When the thiol content of the compounds, according to the invention, prepared in this way is determined analytically, values lower than the value theoretically to be expected are frequently found. It can be presumed that thioether compounds of the formula I, in which $R^1$, in formula I, is thus a radical of the formula

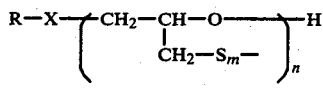

in which m is 0 or 1, are also formed during the reaction at the same time. The compounds which contain thiol groups can, if desired, be isolated in a pure form by means of distillation methods, for example molecular distillation. The reaction products obtained are, however, advantageously used direct. If the thioether content is to be reduced or suppressed, a small amount of a reducing agent, for example zinc dust, can be added during the preparation or after the reaction.

In order to prepare the compounds of the formula I in which $R^1$ is a radical of the formula

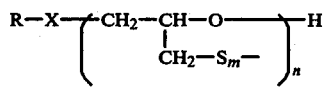

the compounds of the formula II are reacted with alkali metal sulphides $Na_2S_x$ (x = 1–4), especially disodium disulphide.

In this case, the procedure is, in general, that the compounds of the formula II are added to the melt of the alkali metal sulphide $Na_2S_x$ and the mixture is then allowed to react further at a higher temperature, preferably at up to 100° C. In order to remove the alkali metal chloride formed and any excess of alkali metal sulphides which may be present, the reaction mixture is then washed with water and dilute acids and extracted with a suitable solvent, for example ethers, and the solvent is distilled off in order to prepare the product in a pure form.

The reaction can proceed in such a way that a residual content of chlorine is still present in the compounds according to the invention. This has virtually no influence on the desired properties.

The compounds according to the invention can also be prepared by simultaneously reacting an alcohol or mercaptan RXH with epichlorohydrin, $H_2S$ and an alkali metal base, such as NaOH or KOH. Stoichiometric amounts are preferably employed. This embodiment is advantageous since the reaction can be carried out in one reaction vessel.

The compounds of the formula II are obtained according to the process described in U.S. Pat. No. 3,361,723 by adding epichlorohydrin onto alcohols or mercaptans of the formula RXH, in which R and X are as defined above, in the presence of Lewis acids, such as $SbCl_3$, $SnCl_4$, $AlCl_3$ or $BF_3$ as catalysts:

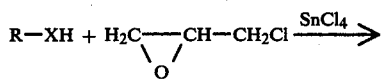

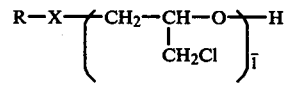

The reaction product is a statistical mixture which can be used as such for the preparation of the compounds according to the invention. An ether comprising molecules of a single type can easily be isolated from the reaction product by distillation methods. It has proved advantageous to use the statistical mixtures themselves.

Thus, in formula I n can assume any value between 0.5 and 8, depending on the ratio in which the reactants are employed for the preparation of the compounds of the formula II and on the reaction conditions chosen.

The compounds according to the invention are of low viscosity or of a viscous to wax-like nature depending on which starting materials are employed and the ratio in which these are employed. The compounds are colorless to slightly yellow colored and surprisingly readily soluble in lubricants, this being the case especially with those compounds in which R in formula I is a branched radical. They are outstandingly suitable as additives for lubricants. In addition to the improvement in the extreme-pressure characteristics, their low corrosive effect should also be mentioned. Surprisingly, because of the good solubility, it is also possible to prepare a master batch.

Even in very small amounts, the compounds of the formula I are effective as extreme-pressure additives in lubricants. Thus, mineral and synthetic lubricating oils, and also mixtures thereof, which are provided with 0.01 to 5% by weight, and preferably 0.05 to 3% by weight, relative to the lubricant, of a compound of the formula I display excellent extreme-pressure lubricating properties which manifest themselves in greatly reduced wear phenomena of the parts to be lubricated. The lubricants which can be used are commonly known to those skilled in the art and are described, for example, in "Schmiermittel Taschenbuch" ("Lubricants Handbook") (Huthig Verlag, Heidelberg, 1974).

The lubricating oil can additionally contain other additives, which are added in order to improve the characteristics, such as antioxidants, metal passivators, rust inhibitors, agents which improve the viscosity index/agents which lower the flow point, dispersing agents/detergents and other extreme-pressure/antiwear additives.

Examples of antioxidants are:

(a) Alkylated and non-alkylated aromatic amines and mixtures thereof, for example: dioctylphenylamine, mono-t-octylphenyl-α- and -β-naphthylamines, phenothiazine, dioctylphenothiazine, phenyl-α-naphthylamine and N,N'-di-sec.-butyl-p-phenylenediamine.

(b) Hindered phenols, for example 2,6-di-tert.-butyl-p-cresol, 4,4'-bis-(2,6-diisopropylphenol), 2,4,6-triisopropylphenol, 2,2'-thio-bis-(4-methyl-6-tert.-butylphenol) and 4,4'-methylene-bis-(2,6-di-t.-butylphenol).

(c) Alkyl phosphites, aryl phosphites or alkaryl phosphites, for example: trinonyl phosphite, triphenyl phosphite and diphenyl decyl phosphite.

(d) Esters of thiodipropionic acid or thiodiacetic acid, for example: dilauryl thiodipropionate or dioctyl thiodiacetate.

(e) Salts of carbamic and dithiophosphoric acids, for example: antimony diamyldithiocarbamate and zinc-diamyldithiophosphate.

(f) Metal salts and metal complexes of organic chelate-forming agents, for example: copper bis-trifluoroacetylacetonate, copper phthalocyanines and the tributyl ester of the monosodium salt of ethylenediaminetetraacetic acid.

(g) Free radical antioxidants, for example nitrogen oxides.

(h) Combinations of two or more antioxidants from amongst the above, for example: an alkylated amine and a hindered phenol.

Examples of metal passivators are:

(a) For copper, for example 1,2,4-triazoles, benzotriazole, tetrahydrobenzotriazole, 2,5-dimercaptothiadiazole, salicylidene-propylenediamine and salts of salicylaminoguanidine, (b) for magnesium, for example: pyridylamines, (c) for lead, for example sebacic acid, quinizarine and propyl gallate, and (d) a combination of two or more of the above additives.

Examples of rust inhibitors are:

(a) Organic acids and their esters, metal salts and anhydrides, for example: N-oleyl-sarcosine, sorbitane-monooleate, lead naphthenate and dodecenylsuccinic anhydride.

(b) Nitrogen-containing compounds, for example:

I. Primary, secondary or tertiary aliphatic or cycloaliphatic amines and amine salts of organic and inorganic acids, for example oil-soluble alkylammonium carboxylates, and II. Heterocyclic compounds, for example: imidazolines and oxazolines.

(c) Phosphorus-containing compounds, for example: amine salts of phosphoric acid partial esters, (d) Sulphur-containing compounds, for example: barium dinonylnaphthalene-sulphonates and calcium petrolenesulphonates, and (e) Combinations of two or more of the above additives.

Examples of agents which improve the viscosity index/agents which lower the flow point are, for example: polymethacrylates, polybutenes, olefine copolymers, polyvinyl-pyrrolidone or polymethacrylate copolymers.

Examples of dispersing agents/detergents are, for example: metal sulphonates and metal phenates (Ca, Ba and Mg) and polybutenyl-succinimides.

Examples of extreme-pressure/anti-war additives are: material containing sulphur and/or phosphorus and/or halogen, for example vegetable oils, zinc-dialkyl-dithiophosphates, tritolyl phosphate and a chlorinated paraffin.

The compounds according to the invention can also be used as PVC stabilizers, either on their own or together with metal stabilizers, or can be used as epoxy curing agents.

The examples which follow serve to illustrate the invention.

(A) Preparation examples

Examples 1 to 6

0.4 ml of tin tetrachloride are added to 0.1 mol of stearyl or octadecyl alcohol. 0.1, 0.3 and 0.5 mol of epichlorohydrin is added dropwise, whilst stirring, at a rate such that the reaction temperature does not exceed 70°–75° C. The reaction mixture is stirred for a further 3 hours at 110 to 115° C. in order to complete the reaction.

The reaction product and 0.1, 0.3 or 0.5 mol of NaOH, dissolved in 150 ml of methanol, are saturated with $H_2S$ and the mixture is heated in an autoclave for 4 hours at 90°–100° C. and under 20–25 atmospheres gauge, whilst stirring. After cooling, the reaction solution is acidified with half-concentrated HCl and the desired product is extracted with ether. The ether solution is dried over $MgSO_4$ and the solvent is then stripped off. The composition of the products obtained and several values determined analytically are given in Table 1. The bar above the indices indicates that these compounds are statistical mixtures.

The SH group content is determined iodometrically and the Cl content and S content are determined by means of elementary analysis.

Table 1

| Example | Compound according to the invention | Residual Cl content in mol % | Total sulphur content | | SH content | | Yield of mercaptan |
|---|---|---|---|---|---|---|---|
| | | | calculated | found | calculated | found | |
| 1 | 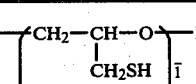 | 0.2 | 11.6 | 8.9 | 11.9 | 10.3 | 86.5 |
| 2 | 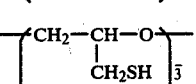 | 0.5 | 21.1 | 20.4 | 21.7 | 20.4 | 94 |
| 3 | 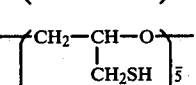 | 0.3 | 25.2 | 24.5 | 25.8 | 23.3 | 90.3 |
| 4 | 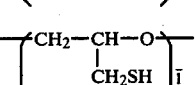 | 0.3 | 8.9 | 8.7 | 9.2 | 8.4 | 91 |
| 5 | 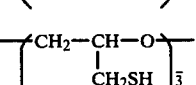 | 3.4 | 19.7 | 14.2 | 18.3 | 11.4 | 64 |
| 6 | 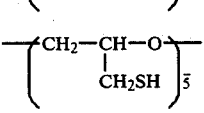 | 1.6 | 22.2 | 20.3 | 22.9 | 17.4 | 76 |

Example 7 to 10

1 mol of Guerbet alcohol (manufacturer: Condea) is reacted with n mols of epichlorohydrin. A methanolic solution of the reaction product and n mols of NaOH is stirred in an autoclave under a $H_2S$ pressure of 10 atmospheres gauge for 1 hour at room temperature. The supply of $H_2S$ is then discontinued and the mixture is stirred for a further 4 hours at 90°–95° C., during which time the pressure rises to 25–30 atmospheres gauge. After cooling, the reaction mixture is washed with dilute HCl and extracted with diethyl ether and this solution is dried over $MgSO_4$, and the solvent is stripped off. The composition of the compounds obtained and some properties are given in Table 2.

distilled off. The resulting epichlorohydrin addition product is then added slowly dropwise to a melt of $Na_2S_2$ at a rate such that a temperature of 50° C. is not exceeded. The mixture is stirred for a further one hour at 80° C., sodium chloride precipitating. The reaction product is then washed successively with water, dilute HCl, dilute NaOH and water and extracted with diethyl ether, the ether solution is dried over $MgSO_4$ and the ether is stripped off. Viscous products which are soluble in universal oils are obtained in yields of more than 90%. The products correspond to the formulae:

 (Example 12)

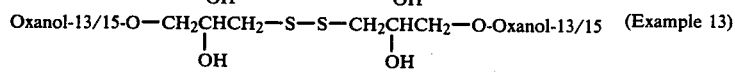 (Example 13)

Table 2

| Example | Compound according to the invention | % SH content | Consistency |
|---|---|---|---|
| 7 | Guerbet-12-O—[CH₂—CH(CH₂SH)—O]₁̄—H | 84 | liquid |
| 8 | Guerbet-12-O—[CH₂—CH(CH₂SH)—O]₂̄—H | 98 | liquid |
| 9 | Guerbet-16/20-O—[CH₂—CH(CH₂SH)—O]₁̄—H | 47 | liquid |
| 10 | Guerbet-16/20-O—[CH₂—CH(CH₂SH)—O]₃̄—H | 83 | liquid |

Example 11

1 mol of Oxanol-13/15 (manufacturer: Ruhr-Chemie), which is a mixture of branched $C_{13}/C_{15}$-alcohols, was reacted in accordance with Example 7 with 1 mol of epichlorohydrin and then with $H_2S/1$ mol of NaOH. The reaction product isolated has a SH content of 51%.

After multiple molecular distillation, a product which has an SH content of 100% is separated off as the first fraction. This product is liquid and oil-soluble to the extent of more than 5%. The second fraction, which has a SH content of less than 15%, has an SH content of more than 70% after reduction with Zn/HCl.

Example 12 and 13

1 mol of i-octanol or Oxanol-13/15 is reacted with 1 mol of epichlorohydrin with the addition of 0.7% of $SnCl_4$, and the alcohol which has not reacted is then

(B) Use example

The following values were determined using the Shell four-ball apparatus (Tentavie method IP 239/69; Extreme pressure and wear lubricant test for oils and greases, four-ball machine).

(1.) I.S.L. = initial seizure load; that is the load under which the oil film collapses within a load period of 10 seconds.

(2.) W.L. = weld load; that is the load under which the 4 balls weld together within 10 seconds.

(3.) "Scar diameter" in mm; that is the average wear diameter after subjection to a load of 70 kg for 1 hour.

(4.) In some cases the corrosive action was also tested by the copper strip test (Cu-St) (the assessment scale extends from 1a to 3b).

Catenex 41 (tradename of Messrs. Shell) was used as the base oil. The results are given in Table 3.

Table 3

| Compound of Example | | Concentration (% by weight) | Cu-St | ISL (kg) | Weld load (kg) | Scar diameter in mm |
|---|---|---|---|---|---|---|
| — | | — | — | 60 | 160 | 2.42 |
| 5 | | 0.1 | 1b | 100 | 205 | 0.94 |
| 9 | | 1.0 | 1a | 110 | 220 | 1.02 |
| 10 | | 0.5 | — | 110 | 205 | 0.99 |
| | | 1.0 | 1b-2a | — | — | — |
| 11 | (SH content = 100%) | 1.0 | 1a | 95 | 220 | 1.98 |
| 12 | | 1.0 | — | — | >200 | 1.1 |
| 13 | | 1.0 | 3b | — | >200 | 1.1 |

What is claimed is:

1. A compound of the general formula I

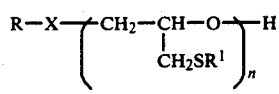 (I)

in which R is linear alkyl having 12 to 24 C atoms, branched alkyl having 8 to 30 C atoms or alkylated phenyl or phenyl-alkyl having 8 to 24 C atoms, X is an oxygen or sulphur atom, n is an integer from 1 to 8 and $R^1$ is a radical of the formula

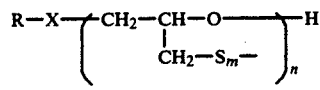

in which m is an integer from 0 to 3.

2. A compound according to claim 1, wherein linear alkyl contains 16 to 24 C atoms, branched alkyl contains 8 to 24 C atoms and the alkylated phenyl or phenyl-alkyl contains 12 to 24 C atoms.

3. A compound according to claim 1, wherein the alkylene group in phenyl-alkyl contains up to 3 C atoms.

4. A compound according to claim 1, wherein the phenyl or phenyl-alkyl is substituted by 1 or 2 alkyl groups which contain 4 to 18 C atoms.

5. A compound according to claim 4, wherein the alkyl groups are branched.

6. A compound according to claim 1, wherein R, in formula I, is branched alkyl.

7. A compound according to claim 1, wherein X is an oxygen atom.

8. A compound according to claim 1, wherein n is a value from 1 to 5.

9. A compound according to claim 1, wherein n is 1 and $R^1$ is a radical of the formula

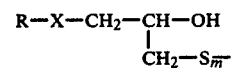

in which m is 0 or 1.

10. A compound according to claim 1, wherein m is 0 or 1.

11. A composition comprising a major amount of a mineral oil lubricant, a synthetic oil lubricant or a mixture thereof and from 0.01 to 5% by weight, relevant to the lubricant, of a compound of formula I according to claim 1.

12. A composition according to claim 11 containing from 0.05 to 3% by weight of a compound of formula I.

13. A compound according to claim 2 wherein the branched alkyl contains 12 to 22 C atoms.

14. A compound according to claim 3 wherein phenyl-alkyl is benzyl.

* * * * *